(12) United States Patent
Mejia et al.

(10) Patent No.: US 8,466,796 B1
(45) Date of Patent: Jun. 18, 2013

(54) BLOOD ALCOHOL INDICATOR DEVICE

(76) Inventors: Wilson Mejia, Glendale, NY (US);
Moises Rodriguez, Bronx, NY (US)

( * ) Notice: Subject to any disclaimer, the term of this patent is extended or adjusted under 35 U.S.C. 154(b) by 629 days.

(21) Appl. No.: 12/713,027

(22) Filed: Feb. 25, 2010

(51) Int. Cl.
*G08B 23/00* (2006.01)

(52) U.S. Cl.
USPC ........................................ 340/576; 340/573.1

(58) Field of Classification Search
USPC .............................................. 340/576, 573.1
See application file for complete search history.

(56) References Cited

U.S. PATENT DOCUMENTS

| | | | |
|---|---|---|---|
| 3,338,087 A | | 8/1967 | Moberg et al. |
| 3,877,291 A | * | 4/1975 | Hoppesch et al. .............. 73/23.3 |
| 4,314,564 A | | 2/1982 | Albarda |
| 4,492,673 A | * | 1/1985 | Eriksen et al. ................... 422/85 |
| 4,749,553 A | * | 6/1988 | Lopez et al. ..................... 422/84 |
| 4,809,810 A | | 3/1989 | Elfman et al. |
| 5,303,575 A | * | 4/1994 | Brown et al. ................... 73/23.3 |
| 5,458,853 A | * | 10/1995 | Porter et al. ..................... 422/84 |
| 6,026,674 A | * | 2/2000 | Gammenthaler ............ 73/19.01 |
| 6,177,051 B1 | * | 1/2001 | Kimelman ....................... 422/85 |
| 6,388,576 B1 | * | 5/2002 | Liu et al. ......................... 340/576 |
| 6,883,364 B2 | | 4/2005 | Sunshine et al. |
| 7,413,047 B2 | * | 8/2008 | Brown et al. .................. 180/272 |
| 7,749,169 B2 | * | 7/2010 | Bayer et al. .................... 600/532 |
| 2007/0093725 A1 | * | 4/2007 | Shaw ............................ 600/543 |
| 2007/0283745 A1 | * | 12/2007 | Pfeiffer ........................... 73/23.2 |
| 2008/0196963 A1 | * | 8/2008 | Karlsson ........................ 180/272 |
| 2009/0205407 A1 | * | 8/2009 | Marhefka et al. .............. 73/23.3 |
| 2009/0278698 A1 | * | 11/2009 | Kamiki ........................... 340/576 |

FOREIGN PATENT DOCUMENTS

| | | |
|---|---|---|
| JP | 2009020598 | 1/2009 |
| WO | WO2007/134040 | 11/2007 |
| WO | WO2008/076310 | 6/2008 |
| WO | WO2009/007844 | 1/2009 |

\* cited by examiner

*Primary Examiner* — Daniel Wu
*Assistant Examiner* — Kam Ma
(74) *Attorney, Agent, or Firm* — Michael I. Kroll

(57) ABSTRACT

A disposable breath analyzing device has a housing with an inlet for receiving a breath sample, chip means for indicating the presence of alcohol, processor means for comparing the alcohol level to a threshold, LED circuit means for illuminating said LED in a steady green for a quantity less than said threshold and blinking red for a quantity greater than said threshold.

3 Claims, 8 Drawing Sheets

BLOOD ALCOHOL INDICATOR DEVICE

BACKGROUND OF THE INVENTION

1. Field of the Invention

Figure 1:
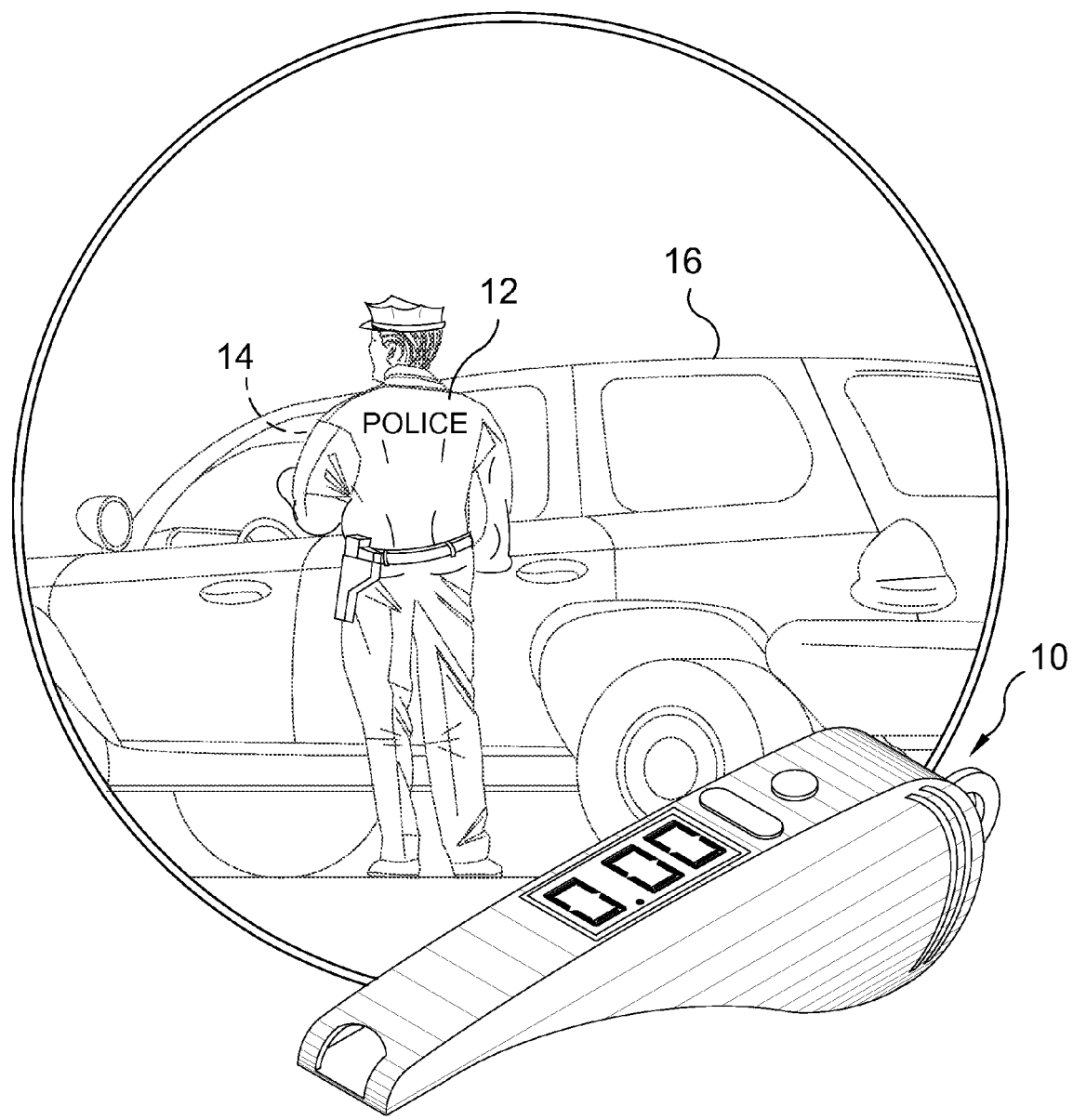

The present invention relates generally to analyzer devices and, more specifically to a portable device for indicating the blood alcohol level through analyzing a user's breath.

The present invention provides both a disposable breath analyzing device and a reusable breath analyzing device.

The disposable breath analyzing device has a housing with an inlet for receiving a breath sample, chip means for indicating the presence of alcohol, processor means for comparing the alcohol level to a threshold, LED circuit means for illuminating said LED in a steady green for a quantity less than said threshold and blinking red for a quantity greater than said threshold.

An alternate embodiment of the present invention provides for a reusable breath analyzer incorporating all of the functions of the disposable embodiment as reusable components and further provides for fastening means for attaching to a set of keys or other personal object.

2. Description of the Prior Art

There are other receptacle designed for bar soap. Typical of these is U.S. Pat. No. 3,338,087 issued to Moberg et al on Aug. 29, 1967.

Another patent was issued to Hoppesch et al. on Apr. 15, 1975 as U.S. Pat. No. 3,877,291. Yet another U.S. Pat. No. 4,314,564 was issued to Albarda on Feb. 9, 1982 and still yet another was issued on Mar. 7, 1989 to Elfman et al. as U.S. Pat. No. 4,809,810.

Another patent was issued to Brown et al. on Apr. 19, 1994 as U.S. Pat. No. 5,303,575. Yet another U.S. Pat. No. 6,177,051 was issued to Kimelman on Jan. 23, 2001. Another was issued to Liu et al. on May 14, 2002 as U.S. Pat. No. 6,388,576 and still yet another was issued on Apr. 26, 2005 to Sunshine et al. as U.S. Pat. No. 6,883,364.

Another patent was published to Wong on Nov. 22, 2007 as International Patent Application Publication No. WO 2007/134040. Yet another International Patent Application Publication No. WO 2008/076310 was published to Williams on Jun. 26, 2008. Another was issued to Ozaki on Jan. 15, 2009 as International Patent Application Publication No. WO 2009/007844 and still yet another was published on Jan. 29, 2009 to Ozaki as Japanese Patent No. JP2009020598.

U.S. Pat. No. 3,338,087

Inventor: E. Milton Wilson

Issued: Aug. 29, 1967

A portable breath analyzing apparatus for determining the presence and concentration of a substance in a breath sample, said apparatus comprising: a) a housing provided with a sample-taking inlet for introducing a sample of breath from a person into said housing and temporarily retaining the sample of breath, b) separator means within said housing for physically separating the substance from other constituents of the breath sample, c) injector valve means in said housing interposed between said sample-taking inlet and said separator means and including a manually operable valve plunger projecting outwardly from said housing for introducing the breath sample into said separator means, d) said valve plunger being normally disposed in a position disconnecting the sample-taking inlet from said separator means but being manually movable with respect to said housing to a second position in which the sample-taking inlet is connected to said separator means, e) means within said housing operably connected to said separator means for detecting the presence of the substance in the breath sample and indicating the concentration of the substance, f) said housing being provided with a chamber in which said detector means and said separator means are enclosed, and g) means controlling the temperature of the chamber in which said detector means and said separator means are enclosed for maintaining said detector means and said separator means at a selected temperature.

U.S. Pat. No. 3,877,291

Inventor: Joseph P. Hoppesch

Issued: Apr. 15, 1975

A breath tester, in two embodiments, employing an alcohol detecting element (e.g. a zinc oxide semiconductor element) which, prior to use, is purged by pumping ambient air across it and maintaining it at a higher than normal operating temperature. In use, after a purging period the air pumping is stopped and the detector heaters are turned off, while breath is directed to the detector and any resulting change in properties (conductivity/resistivity) is sensed and signaled. The first embodiment is largely manually operated and uses a meter to signal both the breath alcohol concentration, and also the purged state of the detecting element. The second embodiment is largely automatic, includes timers and interlocks to prevent misuse, and employs lights to signal its outputs ("fail," for over one BAC level, "warn" for over a lower BAC level and "pass" for under that level) as well as its operational status ("power" on, "wait," "ready," "test"). Both embodiments may be battery powered and means for sensing and signaling the charge level on the batteries is disclosed.

U.S. Pat. No. 4,314,564

Inventor: Scott Albarda

Issued: Feb. 9, 1982

A method and apparatus for determining the alcohol concentration in the blood of a person by testing the person's breath, including, maintaining at least a minimum flow rate for the person's breath to form a test sample of the breath, measuring the alcohol amount in the test sample, measuring the increase in humidity in the test sample over ambient humidity and finding the ratio between the alcohol amount and the increase in humidity. This ratio is proportional to the actual alcohol concentration in the person's blood and cannot be disguised by a person wishing to falsify the results of the test.

U.S. Pat. No. 4,809,810

Inventor: Brian P. Elfman et al.

Issued: Mar. 7, 1989

Disclosed is a system both apparatus and method, for analyzing a breath sample (22). A transducer (24) senses the pressure, temperature and humidity of the breath sample and in response generates a breath signature signal (26). A sensor (28) detects the alcohol of the breath sample and in response generates an alcohol signal (30). Also included is a breath reference (32), and an alcohol reference (34) which includes an alcohol threshold level (36). A first comparator (38) compares the breath signature signal with the breath reference, and in response generates either a valid signal (40) if the signals substantially match or an invalid signal (44) if the signals do not substantially match. A second comparator compares the alcohol signal with the alcohol reference, and in response generates either a passing signal or a failing signal depending on whether or not the threshold level is exceeded.

U.S. Pat. No. 5,303,575

Inventor: Gordon R. Brown

Issued: Apr. 19, 1994

An automated unsupervised apparatus for conducting a blood alcohol level test on an individual user, and subsequently discerning and displaying a meaningful test result, is disclosed. The apparatus comprises an alphanumeric display for instructing the individual user to blow into the apparatus so as to provide a breath sample. A pressure switch is used to monitor the gauge pressure of the individual user's breath sample in order to determine whether the gauge pressure is at or above a threshold value for a predetermined length of time, typically three seconds. The alphanumeric display instructs the individual user to wait and blow again in the event that the gauge pressure does not remain at or above the threshold value for the predetermined length of time. A testing sample of the individual user's breath sample is captured in a fuel cell type alcohol concentration sensor. The alcohol concentration sensor in conjunction with an operational amplifier, a peak circuit detector and an analogue to digital convertor, effects an automated electrochemical analysis of the testing sample. A measurement value of the alcohol of the testing sample is produced, and introduced into a microprocessor, where a numeric value derived from the measurement value and related to the individual user's blood alcohol level, is calculated. The alphanumeric display displays this numeric value and the category corresponding to the numeric value as being one of "pass", "warn", and "fail".

U.S. Pat. No. 6,177,051

Inventor: Rosemarie L. Kimelman

Issued: Jan. 23, 2001

A dispensable alcohol breath analyzer system including a rectilinear box with an analyzer on one face and an extendable tube on another face. The system also includes a plurality of units located within the box to be dispensed, each unit containing an analyzer and a sanitary wrapper therearound. The indicator includes a cylindrical alcohol indicator and an associated rotatable indicator arrow. A gauge is provided whereby the increased of alcohol permeates through the indicator to rotate the arrow to an extent corresponding to the percent of alcohol within the breath detected. The second indicator includes a diaphragm through which the user's breath may flow to exterior of the device and an associated color gauge thereadjacent whereby the diaphragm will change colors as a function of the percent of alcohol in the breath of the user for being compared with the color on the gauge.

U.S. Pat. No. 6,388,576

Inventor: Ko-Chien Liu

Issued: May 14, 2002

A minitype alcohol excessive warning device includes a detecting circuit consisting of a power circuit, a delay circuit, and a sensing circuit. The detecting circuit is mounted in a housing having a simple structure, thereby constructing a miniature alcohol excessive warning device. In such a manner, the minitype alcohol excessive warning device has a low cost, can be used easily and conveniently, and is portable.

U.S. Pat. No. 6,883,364

Inventor: Steven A. Sunshine

Issued: Apr. 26, 2005

A vapor sensing device that is sufficiently small and lightweight to be handheld, and also modular so as to allow the device to be conveniently adapted for use in sensing the presence and concentration of a wide variety of specified vapors. The device provides these benefits using a sensor module that incorporates a sample chamber and a plurality of sensors located on a chip releasably carried within or adjacent to the sample chamber. Optionally, the sensor module can be configured to be releasably plugged into a receptacle formed in the device. Vapors are directed to pass through the sample chamber, whereupon the sensors provide a distinct combination of electrical signals in response to each. The sensors of the sensor module can take the form of chemically sensitive resistors having resistances that vary according to the identity and concentration of an adjacent vapor. These chemically sensitive resistors can each be connected in series with a reference resistor, between a reference voltage and ground, such that an analog signal is established for each chemically sensitive resistor. The resulting analog signals are supplied to an analog-to-digital converter, to produce corresponding digital signals. These digital signals are appropriately analyzed for vapor identification.

International Patent Application Publication No. WO 2007/134040

Inventor: Chi Wing Wong

Issued: Nov. 22, 2007

The present invention relates to a portable, personal breath tester device for testing the blood alcohol level of the user of the device. The breath tester comprises a circuit board, wherein a sensor, a liquid crystal display, and a processing unit are installed on and electrically connected to the circuit board. The processing unit receives a voltage signal from the sensor representing the blood alcohol level of the user and converts the voltage signal to a precise value that is displayed on the liquid crystal display.

International Patent Application Publication No. WO 2008/076310

Inventor: Barry Williams

Published: Jun. 26, 2008

A method and an apparatus is provided for a self-service breathalyzer kiosk system for collecting and reporting blood alcohol level information. The system and method enables a user to submit a report containing the user's current blood alcohol level at the time the report is submitted. In particular, the kiosk may be used to collect the current blood alcohol level information of the user and transmit the report of the current blood alcohol level information of the user over a communication network.

International Patent Application Publication No. WO 2009/007844

Inventor: Osamu Ozaki

Published: Jan. 15, 2009

A breathalyzer test device (1) includes vigilance detecting means (10) for detecting the vigilance of a test subject, and breathalyzer test means (11, 30) for performing a breathalyzer test on the subject based on the vigilance detected by the vigilance detecting means (10).

Japan Patent Number JP2009020598

Inventor: Osamu Ozaki

Issued: Jan. 29, 2009

To provide a drunk driving preventing apparatus for reducing the burden of a driver in a breathalyzer test. SOLUTION: The drunk driving preventing apparatus 1 comprises an ECU 2 for controlling an actuation unit 6, in which an ignition sensor 3, a breathalyzer 4, and a personal authentication device (personal identifying means) 5 are connected to the ECU2. The ECU 2 comprises a timer 21, a drunk driving prevention processing unit 22 for performing a drunk driving prevention process, and a breath test determination processing unit 23 for disabling the drunk driving prevention process under a predetermined condition. The breath test determination processing unit 23 disables the drunk driving prevention process to be performed by the drunk driving prevention processing unit 22 within a predetermined time from an engine stop.

While these breath analyzers may be suitable for the purposes for which they were designed, they would not be as suitable for the purposes of the present invention, as hereinafter described.

SUMMARY OF THE PRESENT INVENTION

A primary object of the present invention is to provide a breath analyzing device for measuring the amount of alcohol in a breath sample.

Another object of the present invention is to provide a breath analyzing device for measuring the amount of alcohol in a breath sample wherein said device is disposable.

Yet another object of the present invention is to provide a breath analyzing device for measuring the amount of alcohol in a breath sample wherein said device is reusable.

Still yet another object of the present invention is to provide a disposable breath analyzing device having housing with an inlet for introducing a breath sample.

An additional object of the present invention is to provide a disposable breath analyzing device having housing with an external illuminable element for indicating the results of an analysis of said breath sample.

A further object of the present invention is to provide a disposable breath analyzing device having a housing incorporating a chip for measuring the amount of alcohol with said breath sample.

A still yet further object of the present invention is to provide a disposable breath analyzing device having a processor for comparing the chip results to a threshold value.

Another object of the present invention is to provide a disposable breath analyzing device having an LED circuit means for illuminating one of a green LED and one of a red LED.

Yet another object of the present invention is to provide a disposable breath analyzing device having an LED circuit means for steadily illuminating said green LED when the breath sample is below said threshold value.

Still yet another object of the present invention is to provide a disposable breath analyzing device having an LED circuit means for steadily illuminating said green LED when the breath sample is below said threshold value.

Additional objects of the present invention will appear as the description proceeds.

The present invention overcomes the shortcomings of the prior art by providing a disposable breath analyzing device and a reusable breath analyzing device. The disposable breath analyzing device has a housing with an inlet for receiving a breath sample, chip means for indicating the presence of alcohol, processor means for comparing the alcohol to a threshold, LED circuit means for illuminating said LED in a steady green for a quantity less than said threshold and blinking red for a quantity greater than said threshold. An alternate embodiment of the present invention provides for a reusable breath analyzer incorporating all of the functions of the disposable embodiment as reusable components and further provides for fastening means for attaching to a set of keys or other personal object.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

Figure 2:
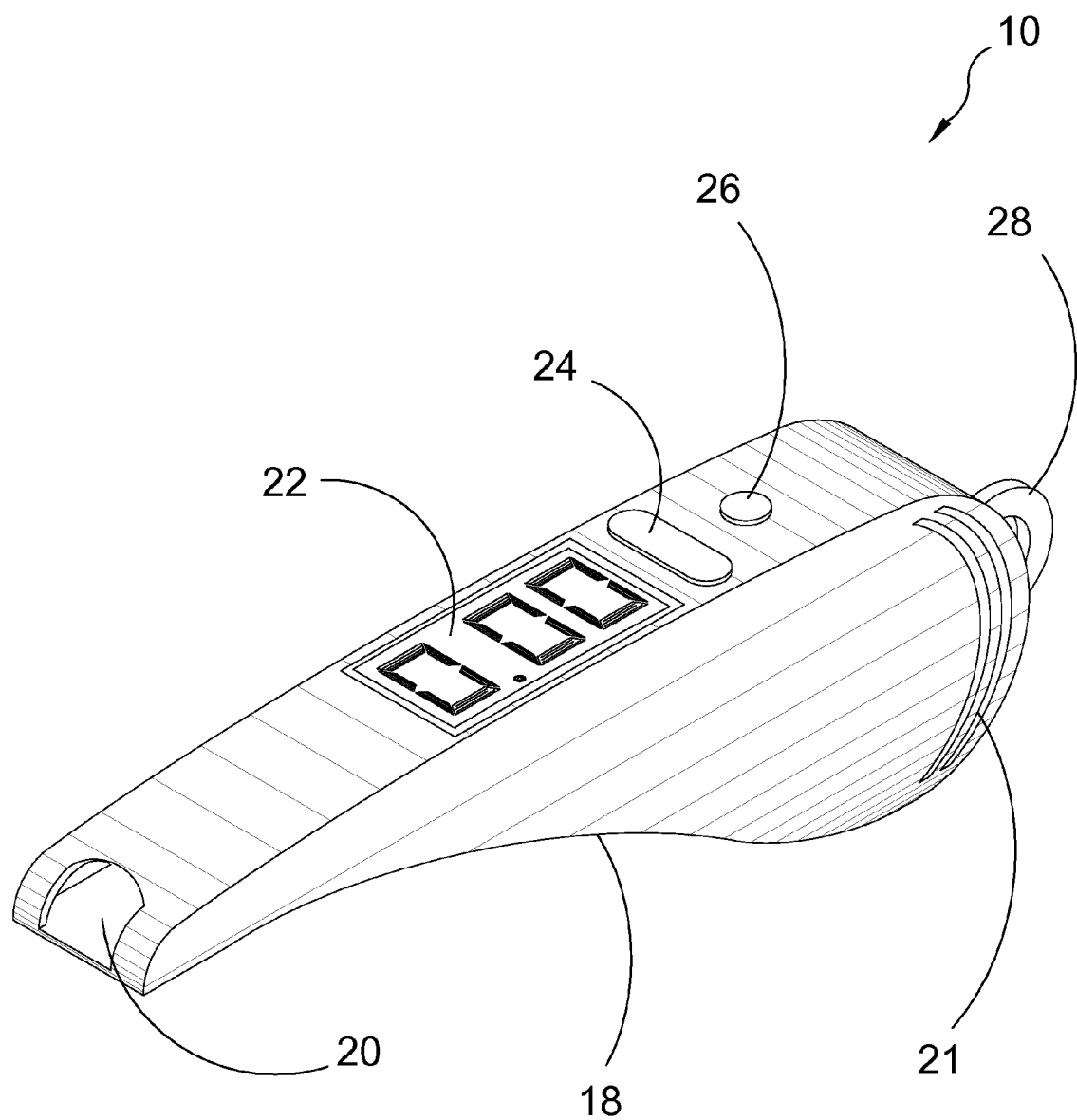
Figure 3:
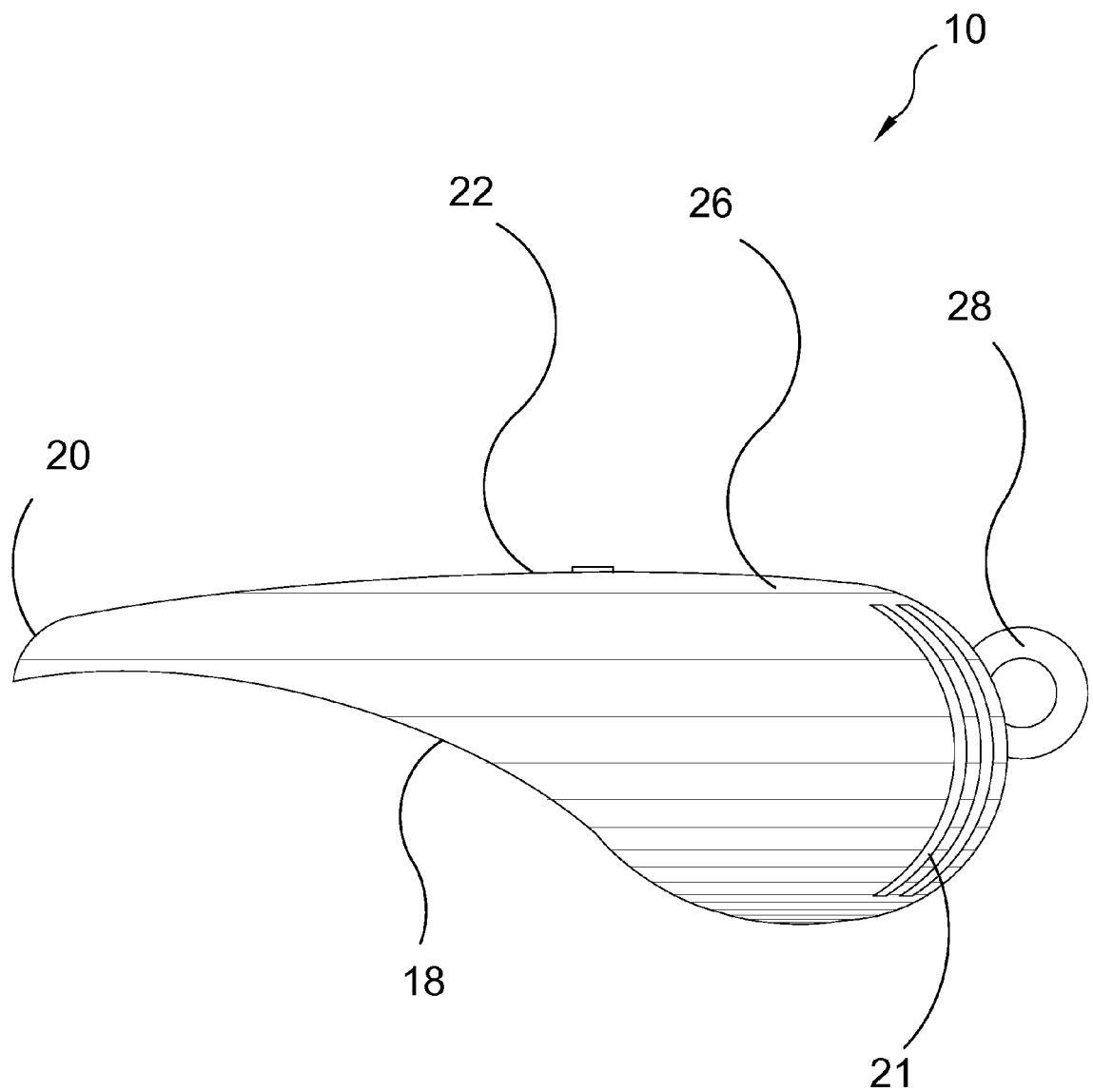
Figure 4:
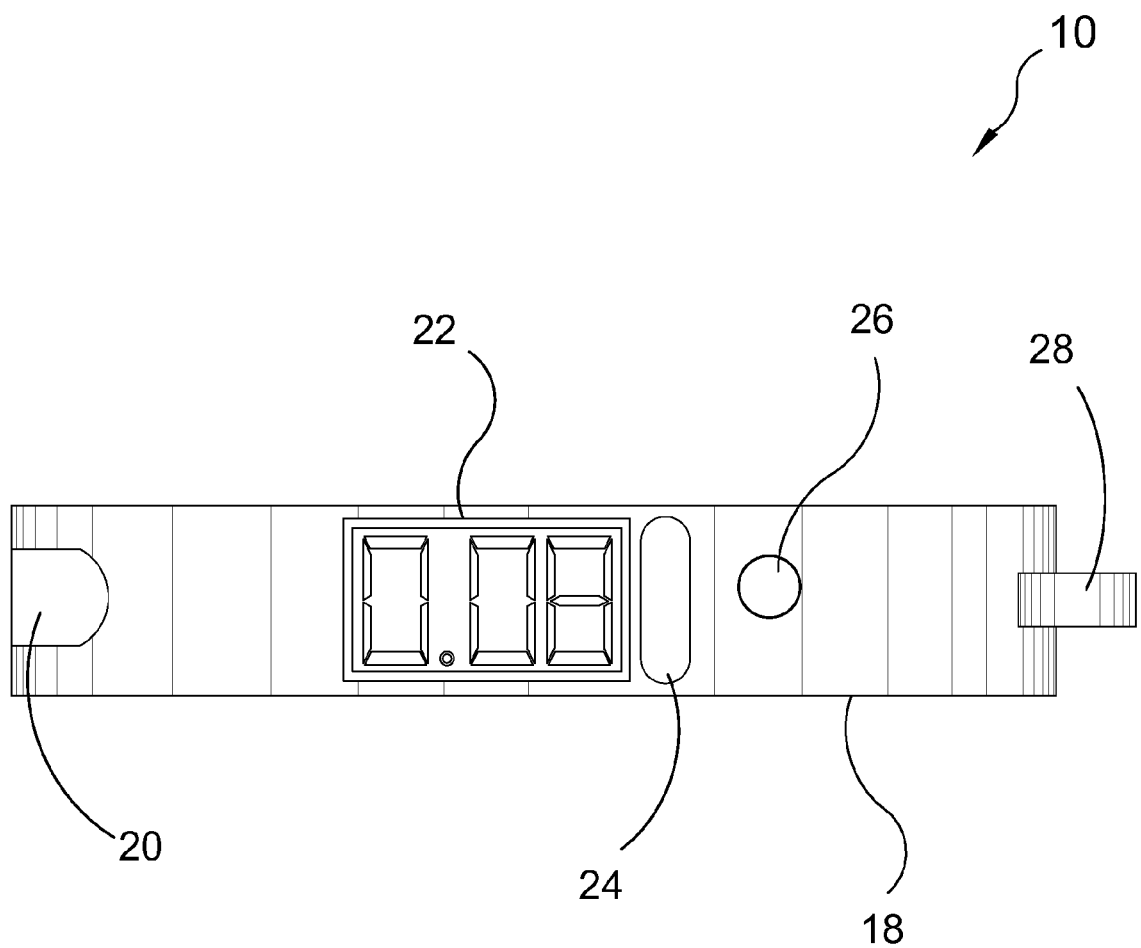
Figure 5:
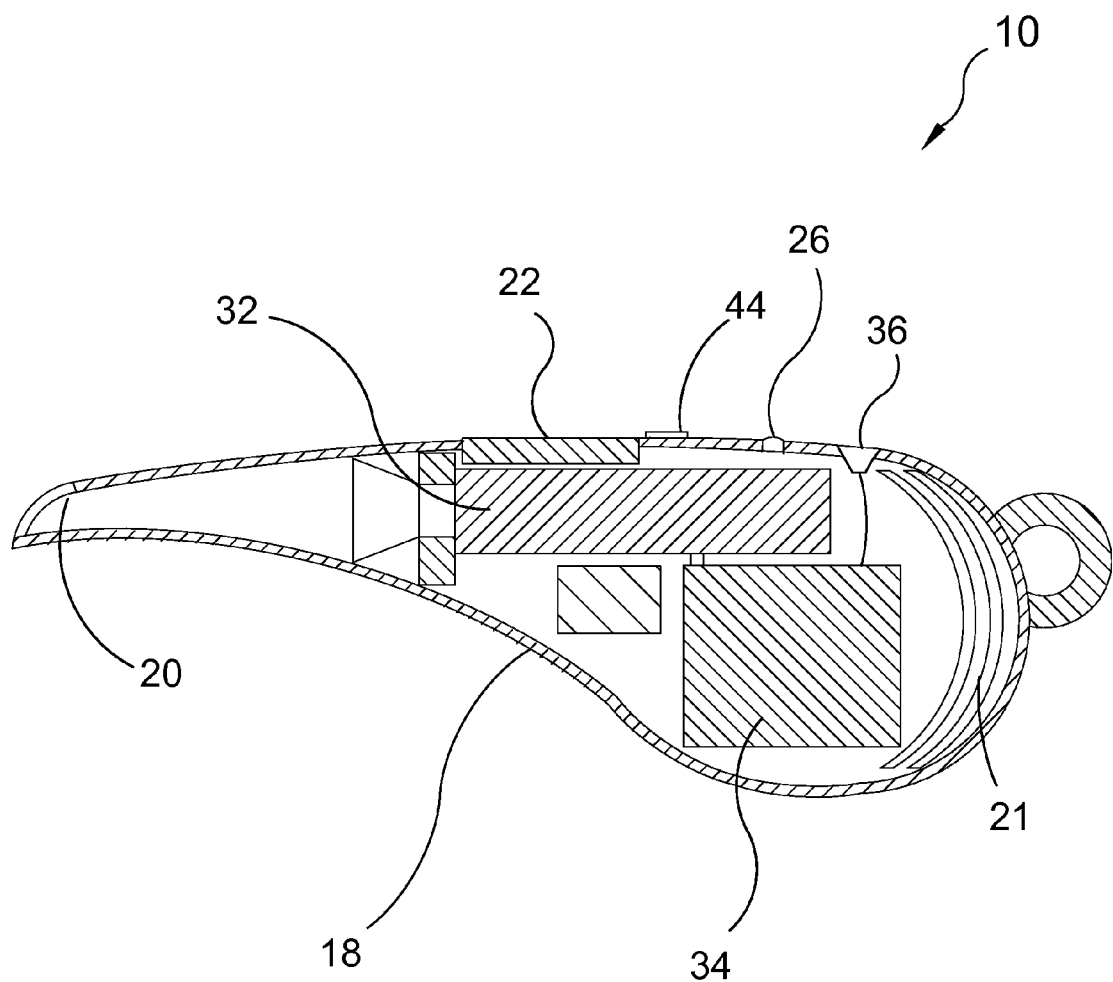
Figure 6:
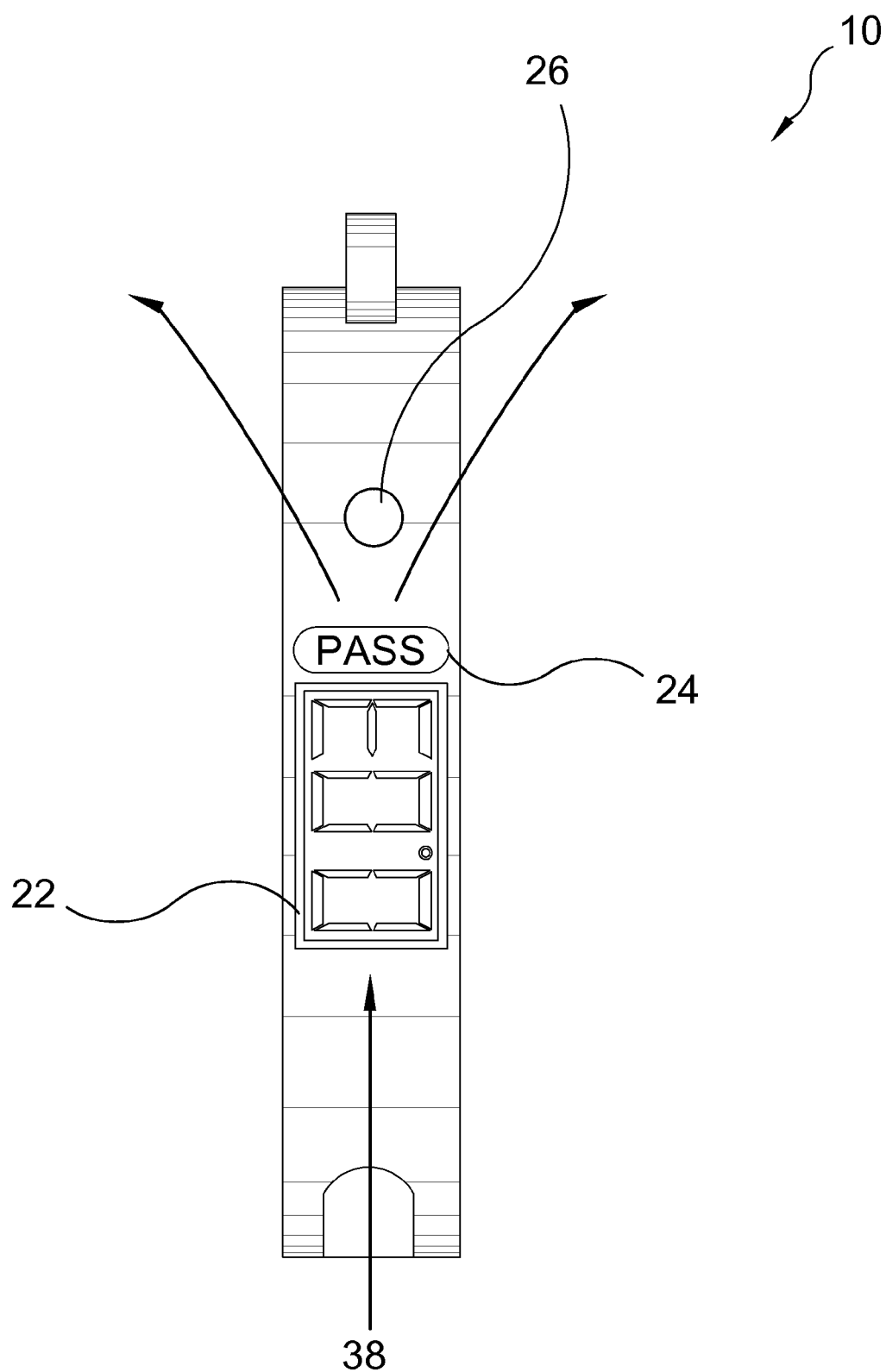
Figure 7:
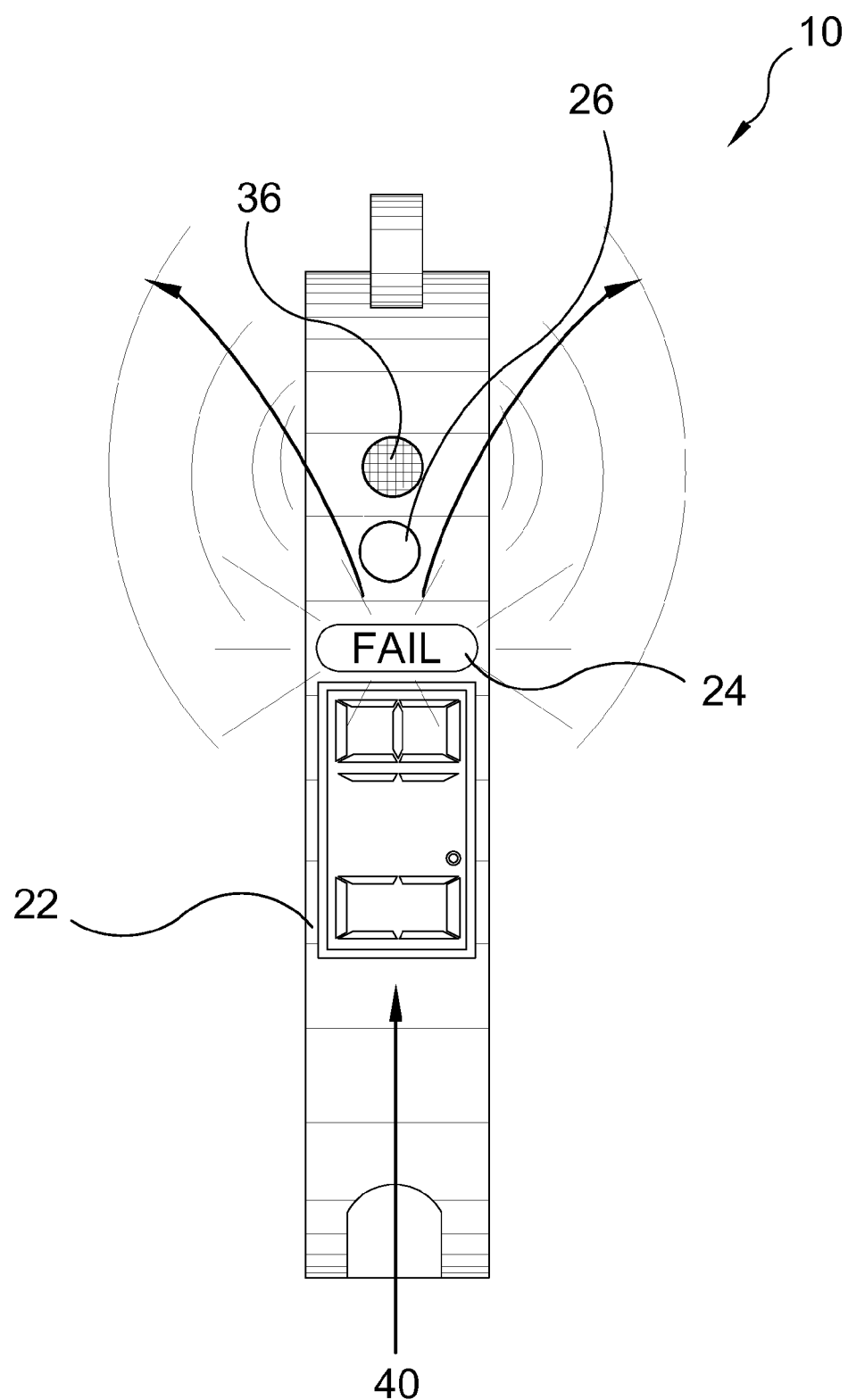
Figure 8:
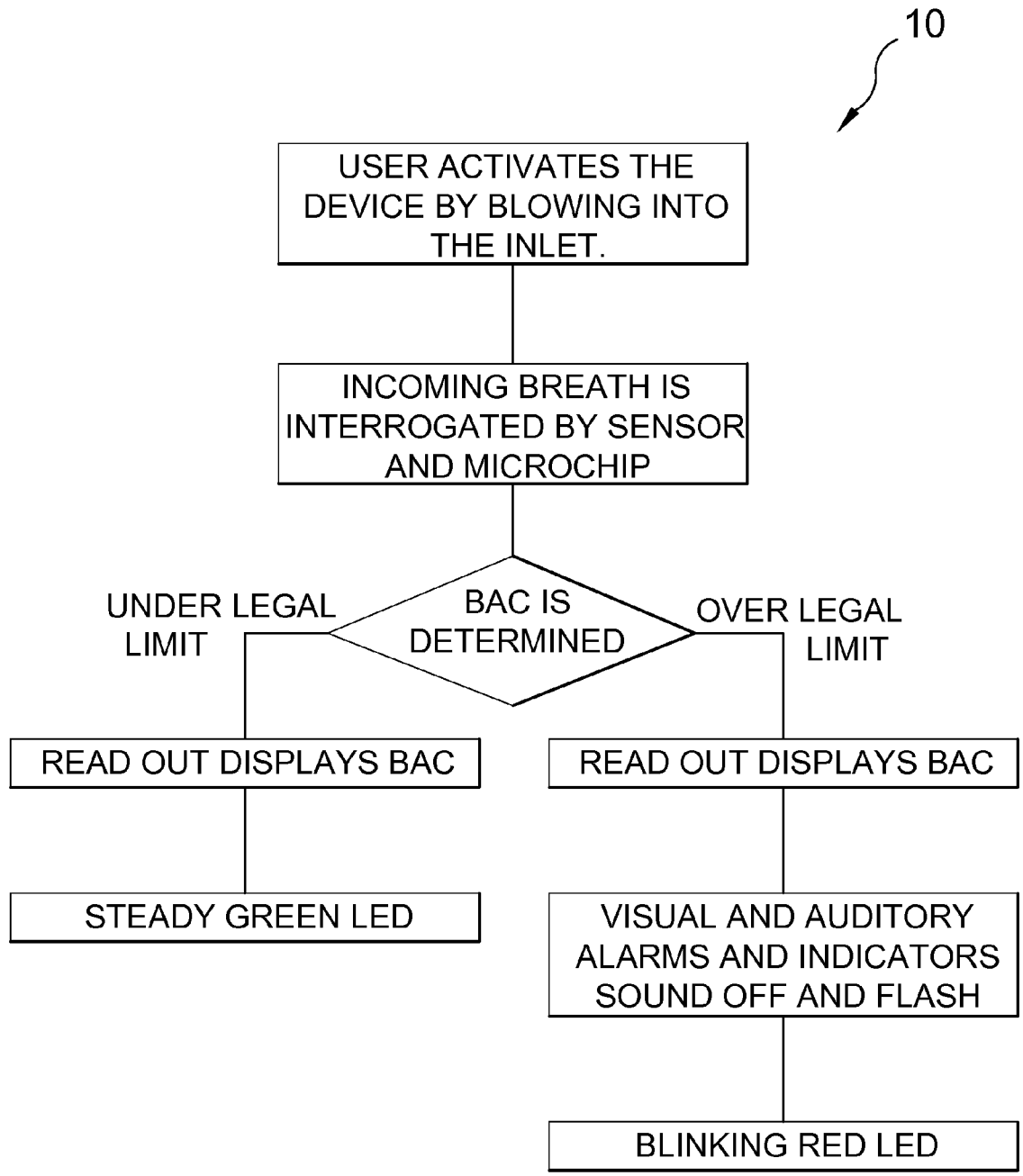

In order that the invention may be more fully understood, it will now be described, by way of example, with reference to the accompanying drawing in which:

FIG. 1 is an illustrative view of the present invention in use.
FIG. 2 is an illustrative view of the present invention.
FIG. 3 is a side view of the present invention.
FIG. 4 is a top view of the present invention.
FIG. 5 is a sectional view of the present invention.
FIG. 6 is a sectional view of the present invention.
FIG. 7 is a sectional view of the present invention.
FIG. 8 is a flow chart of the present invention.

DESCRIPTION OF THE REFERENCED NUMERALS

Turning now descriptively to the drawings, in which similar reference characters denote similar elements throughout the several views, the figures illustrate the Blood Alcohol Content Indicator Device of the present invention. With regard to the reference numerals used, the following numbering is used throughout the various drawing figures.

10 Blood Alcohol Content Indicator Device
14 police officer
16 motor vehicle
18 housing
20 inlet
21 egress vents
22 numerical display"
24 status display
26 LED
28 key ring loop
30 interior of 18
32 sensor
34 microchip
36 audible indicator
38 sober breath
40 intoxicated breath

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of the blood alcohol content (BAC) indicator device 10 of the present invention in use. The BAC indicator device 10 is a small indicator device that may be attached to one's key chain whereby a user may blow into an opening so that said user's breath will be interrogated to return an accurate reading to the user of the users BAC or (blood alcohol content). Shown is a police officer 12 administering a breath analysis with the present invention to the driver 14 of a motor vehicle 16.

FIG. 2 is an illustrative view of the BAC indicator device 10 of the present invention. The BAC indicator device 10 comprises a housing 18 with a substantially hollow interior, an inlet 20 disposed on a front portion thereof, a plurality of rearwardly positioned vents 21 on each side thereof, a digital numerical display 22, a status display 24, an LED 26 and a key ring loop 28.

FIG. 3 is a side view of the present invention. Shown is a side view of the BAC indicator device 10 demonstrating the positioning of the inlet 20, vents 21, numerical display 22, LED 26 and key ring loop 28 on the housing 18.

FIG. 4 is a top view of the present invention. Shown is a top view of the BAC indicator device 10 demonstrating the positioning of the inlet 20, vents 21, numerical display 22, status display 24, LED 26 and key ring loop 28 on the housing 18.

FIG. 5 is a sectional view of the present invention. Shown is sectional side view of the BAC indicator device showing the primary components thereof. The user blows into the inlet 20 and the air passes through the interior 30 of the housing 18 where it comes in content with a sensor 32 communicating with a microchip 34 that analyzes the BAC and responds accordingly. A predetermined BAC is programmed into the microchip 34. The numerical display 22 indicates the reported level and the status display 24 displays "PASS" or "FAIL" accordingly. The LED 26 turns green upon a passing analysis and red upon failing. An optional audible indicator 36 is enabled when a failed result is detected. The air flow is expelled through a plurality of vents 21.

FIG. 6 is a sectional view of the present invention. Shown is the BAC indicator device 10 being utilized and activated by blowing into the inlet 20 . . . . The sober breath 38 passes and is indicated by the numerical display 22, the status display 24 and the LED 26.

FIG. 7 is a sectional view of the present invention. Shown is the BAC indicator device 10 being utilized and activated by blowing into the inlet 20 . . . . The intoxicated breath 40 fails and is indicated by the numerical display 22, the status display 24, the audible indicator 36 and the LED 26.

FIG. 8 is a flow chart of the BAC indicator device 10 of the present invention. Shown is a flow chart depicting the course of action taken by the individual components comprising the present invention while in use.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A portable blood alcohol content indicator device for determining the blood alcohol of an individual comprising:
   a) a housing having a substantially hollow interior portion, a front portion and a rear portion, said front portion being narrowed down from said rear portion;
   b) an inlet at said front portion leading into said interior portion for receiving exhaled breath of said individual;
   c) a plurality of vents disposed at said rear portion of and along both sides of said housing for expelling air flow from said housing;
   d) a sensor, communicating with a microchip, for detecting and measuring the alcohol content of air passing through said interior portion, said sensor being disposed in said interior portion and in line with flow of air through said housing;
   wherein said microchip being programmed to compare the alcohol content measured by said sensor with a predetermined threshold;
   e) a plurality of indicators communicating with said microchip externally situated in a row on a top outer surface of said housing;
   f) said plurality of indicators comprising a digital numerical display for indicating the value of the alcohol content, a status display that reads "PASS" or "FAIL" according to said comparison, an LED, and an audible indicator, said LED being green or red to indicate passing condition or failing condition, respectively according to said comparison, said audible indicator being activated when the failing condition is detected; and g) a key ring loop mounted on said rear portion of said housing adjacent and between said vents on both sides of said rear portion for fastening a key chain thereto.

2. The blood alcohol content indicator device according to claim 1, wherein said blood alcohol indicator device is disposable.

3. The blood alcohol content indicator device according to claim 1, wherein said blood alcohol indicator device is reusable.

* * * * *